United States Patent [19]

Mitsuhashi et al.

[11] Patent Number: 4,994,556
[45] Date of Patent: Feb. 19, 1991

[54] NOVEL LYMPHOKINE AND ITS PRODUCTION AND USES

[75] Inventors: Masakazu Mitsuhashi; Masashi Kurimoto, both of Okayama, Japan

[73] Assignee: Kabushiki Kaisha Hayashibara Seibutsu Kagaku, Okayama, Japan

[21] Appl. No.: 904,864

[22] Filed: Sep. 8, 1986

[30] Foreign Application Priority Data

Sep. 18, 1985 [JP] Japan ................ 60-205537

[51] Int. Cl.$^5$ .................. C07K 15/00; A61K 39/00
[52] U.S. Cl. .................. 530/351; 530/827; 530/837; 530/828; 424/85.1; 424/85.2; 424/85.4; 424/85.5; 424/85.6; 424/85.7; 514/2; 514/8; 514/21; 435/70.1
[58] Field of Search ............... 530/351, 827, 837, 828; 514/2, 21, 8; 424/85.1-85.7; 435/68, 70.1

[56] References Cited

U.S. PATENT DOCUMENTS 4,758,549 7/1988 Mitsuhashi et al. .............. 514/8

FOREIGN PATENT DOCUMENTS 146293 8/1983 Japan .
146228 7/1985 Japan .
2117385 2/1983 United Kingdom .
2153364 8/1985 United Kingdom .

OTHER PUBLICATIONS

E. A. Carswell et al., Proceedings of the National Academy of Sciences of the U.S.A., vol. 72, No. 9, pp. 3,666-3,670 (1975).
Lymphokines, vol. 2, pp. 235-272, "Tumor Necrosis Factor", Edited by E. Pick, Published by Academic Press, Inc. (1981).
Ryuichi Aoki et al. Shin-Menekigaku Sosho, vol. 6, "Lymphokine", pp. 87-105 (1979), Published by Igaku-Shoin, Tokyo (With Partial Translation).
In Vitro Methods in Cell-Mediated Immunity, Edited by B. R. Bloom & P. R. Glade, Published by Academic Press, Inc. (1971).
Cellular Immunology, vol. 38, pp. 388-402 (1978).

*Primary Examiner*—Garnette D. Draper
*Attorney, Agent, or Firm*—Browdy and Neimark

[57] ABSTRACT

A novel lymphokine and its production and uses are disclosed. The lymphokine is a glycoprotein with a molecular weight of 15,000±2,000 daltons; isoelectric point pI, 4.5±0.5; electrophoretic mobility Rf, 0.73±0.05; cytotoxic on L 929 cell; and cytostatic on KB cell with or without human interferon-alpha. The lymphokine significantly inhibits in vivo the growth of malignant human tumors in cooperation with human interferon, therefore is useful in prophylactic and therapeutic treatment of human malignant tumors.

8 Claims, No Drawings

NOVEL LYMPHOKINE AND ITS PRODUCTION AND USES

FIELD OF THE INVENTION

The present invention relates to a novel lymphokine, as well as to its production and uses.

ABBREVIATIONS

LT is the abbreviation of lymphotoxin; TNF, tumor necrosis factor; IL, interleukin; IFN, interferon; IFN-alpha, interferon-alpha; IFN-gamma, interferon-gamma: and HuIFN, human-specific interferon.

BACKGROUND OF THE INVENTION

LT and TNF are known as lymphokines which damage tumor cells. For example, LT is described in Ryuichi Aoki et al., SHIN-MENEKIGAKU SOSHO, Vol.6, "Lymphokine", pp.87-105 (1979), published by Igaku-Shoin, Tokyo, In Vitro Method in Cell-Mediated Immunity, edited by B. R. Bloom & P. R. Glade, published by Academic Press, Inc. (1971), and Cellular Immunology, Vol.38, pp.388-402 (1978); and TNF is described in E. A. Carswell et al., Proceedings of the National Academy of Sciences of the U.S.A., Vol.72, No.9, pp.3,666-3,670 (1975), and Lymphokines, Vol.2, pp.235-272, "Tumor Necrosis Factor", edited by E. Pick, published by Academic Press, Inc. (1981).

Recently, H. Ohnishi et al. disclosed an antioncotic lymphokine glycoprotein in Japanese Patent Laid-Open No. 146,293/83, while we disclosed an antioncotic glycoprotein in Japanese Patent Laid-Open No.126,228/85.

DETAILED DESCRIPTION OF THE INVENTION

We have studied lymphokines over a period of years. As the result, we discovered a novel lymphokine with physicochemical properties entirely different from those of known lymphokines, and its cytotoxic activity on malignant tumor cells in the presence of IFN. We established the production and uses of the lymphokine.

More particularly, the present invention relates to a novel lymphokine possessing the following physicochemical properties:

(1) Molecular weight; 15,000±2,000 daltons
(2) Isoelectric point; pI=4.5±0.5
(3) Electrophoretic mobility: on Disc-PAGE, Rf=0.73±0.05
(4) uv-Absorption spectrum; an absorption maximum at a wave length of about 280 nm
(5) Solubility in solvents: dissoluble in water, saline and phosphate buffer scarcely dissoluble or insoluble in ethyl ether, ethyl acetate or chloroform
(6) Coloring reaction; protein-positive by the Lowry's method or microburette method saccharide-positive by the phenol-sulfuric acid method or anthrone-sulfuric acid method
(7) Biological activities; cytostatic on KB cell with or without HuIFN-alpha cytotoxic on L 929 cell substantially free of IL and IFN activities
(8) Stability in aqueous solution; stable up to 60° C when incubated at pH 7.2 for 30 minutes stable in the pH range of 2.0-11.0 when incubated at 4° C for 16 hours, and
(9) Stability on cryopreservation; stable at $-10°$ C over a period of one month or longer.

Also, the present invention relates to the production and uses of the lymphokine.

The novel lymphokine will be designated simply as "LK 3" hereinafter.

LK 3 is produced by exposing an LK 3 producing human cell, for example, human leukocyte, human lymphocyte and established cell lines thereof, to an LK 3 inducer. Human leukocyte and lymphocyte can be isolated from fresh human blood. The established human cell line can be proliferated with conventional in vitro method.

For a more efficient practice of the present invention, it is desirable to employ an in vivo cell proliferation procedure wherein the above described human cell line is transplanted directly to a non-human warm-blooded animal, or, alternatively, inoculated in a conventional-type diffusion chamber by which the nutrient body fluid of a non-human warm-blooded animal is supplied to the cell line.

Unlike in vitro cell proliferation, the in vivo procedure is characterized in that it requires no or much less nutrient culture medium containing expensive serum and less cares during the cell proliferation, and still that the human cells proliferated by the procedure give a much higher LK 3 activity.

In the in vivo procedure, the human cell line can be easily proliferated while utilizing the nutrient body fluid supplied from a non-human warm-blooded animal by transplanting the human cell line to a non-human warm-blooded animal, or, alternatively, placing the cell line in a conventional-type diffusion chamber devised to receive the body fluid, and embedding or placing the chamber in or on the animal. In either case, the animals are fed in usual manner.

Furthermore, the in vivo procedure is characterized by the additional features that a much more stabilized and rapid cell proliferation, a higher cell production, and an extremely higher LK 3 production per cell are attained than with the in vitro procedure.

The human cell lines usable in the invention may be those which are LK 3-producible, transplantable to a non-human warm-blooded animal, and readily proliferatable in the animal. For example, the human cell lines listed in Protein, Nucleic Acid and Enzyme, Vol.20, No.6, pp.616-643 (1975) are employable in the invention. Specifically suited are human lymphoblastoid lines, such as Namalwa (ATCC CRL 1432), as described in Journal of Clinical Microbiology, Vol.1, pp.116-117 (1975); BALL-1, TALL-1 and NALL-1, as described by I. Miyoshi, Nature, Vol.267, pp.843-844 (1977); M-7002 and B-7101, as described in The Journal of Immunology, Vol.113, pp.1,334-1,345 (1974); JBL, EBV-Sa, EBV-Wa, MOLT-3 (ATCC CRL 1552) and EBV-HO, as described in The Tissue Culture, Vol.6, No.13, pp.527-546 (1980); CCRF-SB (ATCC CCL 120); CCRF-CEM (ATCC CCL 119); BALM 2; DND-41; and other established cell lines obtained by transforming normal human monocyte or granulocyte with any carcinogenic virus, agent or radiation.

The proliferation rate and/or LK 3 productivity per cell of these cell lines may be improved by cell fusion technique using polyethylene glycol or Sendai virus, or by gene recombinant technique using nuclease enzyme, ligase enzyme, DNA polymerase enzyme, etc. The listing of the employable human cell lines in the SPECIFICATION shall not be intended in any way to limit the scope of the invention. One or more members of these cell lines may be used in combination in the steps up to the LK 3 induction which will be described hereinafter. If necessary, human leukocyte or lymphocyte which can be obtained from fresh human blood may be used in combination with any of the human cell lines.

The non-human warm-blooded animal usable in the invention may be one of those wherein such human cell is proliferatable. Examples of such animals are fowls such as chicken and pigeon; and mammals such as dog, cat, monkey, rabbit, goat, pig, horse, cow, guinea pig, rat, nude rat, hamster, mouse and nude mouse.

Since transplantation of the human cell to the animal elicits undesirable immunoreaction, the use of a nonhuman warm-blooded animal in the possible youngest stage, for example, egg, embryo or fetus, or newborn or infant animal, is desirable in order to reduce such immunoreaction as far as possible.

Prior to the transplantation, the animal may be irradiated with x-ray or gamma-ray, about 200–600 rem, or injected with an antiserum or an immunosuppressant to reduce the immunoreaction to the possible lowest level.

When an immunodeficient animal such as nude mouse and nude rat is used as the host animal, any of the aforementioned human cell lines can be transplanted in these animals without such pretreatment, and proliferated readily with less fear of causing undesirable immunoreaction because these animals exhibit less immunoreaction even in their adulthood.

One can stabilize cell proliferation and/or augment LK 3 production by successive transplantation using the same or different non-human warm-blooded animals. These objectives can be attained by, for example, first transplanting a human cell line to a hamster and proliferating the human cell line in the hamster, then successively transplanting the proliferated human cell to a nude mouse. The successive transplantation may be carried out with a non-human warm-blooded animal of the same class or order, as well as those of the same species or genus.

The human cell can be transplanted in any site of the animal as long as the human cell proliferates in the site: for example, in the allantoic cavity, or intravenously, intraperitoneally or subcutaneously.

Alternatively, the human cell is proliferated by placing it in a conventional diffusion chamber of various shapes and sizes, equipped with a suitable means which prevents contamination of the chamber with the animal cell, but supplies the human cell with the nutrient body fluid of the animal, for example, membrane filter, ultrafilter or hollow fiber of a nominal pore size of about $10^{-7}-10^{-5}$ m; embedding, for example, intraperitoneally, the chamber in the animal; and allowing the human cell to proliferate in the chamber while receiving the nutrient body fluid from the animal.

Furthermore, the diffusion chamber can be designed and placed, for example, on the animal, so that the nutrient fluid in the chamber can circulate freely through the chamber. The culture in the chamber can be observed during the cell proliferation through transparent side window means, equipped on the chamber wall(s), and/or the chamber per se can be replaced at intervals with a fresh one both to continue the cell proliferation over the period of the life span of the animal without sacrificing and to augment much more the cell production per animal. Since due to the absence of direct contact of the human cell with the animal cell such diffusion chamber elicits much less undesirable immunoreaction, any non-human warm-blooded animal may be readily used without pretreatment to reduce such immunoreaction, and the proliferated viable human cell can be harvested easily from the diffusion chamber.

Feeding of the animal can be carried out in usual manner, and no special care is required even after the transplantation. The period required to obtain maximum cell proliferation is generally from 1 to 10 weeks. The number of the human cell so obtained is about $10^7-10^{12}$ cells per animal or more. More particularly, according to the invention, the transplanted human cell increases to about $10^2-10^7$-fold or more, which is about $10-10^6$-fold or higher than that obtained by inoculating and proliferating the human cell on an in vitro nutrient culture medium. This is very favorable in the production of LK 3.

Any method is employable in the invention as long as LK 3 production can be induced in the proliferated human cell therewith. The proliferated human cell can be exposed in the animal, used as the host for cell proliferation, to an LK 3 inducer. For example, a human cell, proliferated in ascite in suspension, or a tumor cell, formed, for example, subcutaneously, is directly exposed in vivo to an LK 3 inducer to induce LK 3 production, and the accumulation of LK 3 is harvested from the ascite, serum and/or tumor, followed by purification of the LK 3. Alternatively, the proliferated human cell is harvested from the animal and then exposed in vitro to an LK 3 inducer. For example, the proliferated human cell, obtained by harvesting from ascite suspension, or extracting and disaggregating the tumor mass(es), formed, for example, subcutaneously, is suspended in a nutrient culture medium, prewarmed to a temperature of about 20–40° C, to give a cell density of about $10^5-10^8$ cells/ml, and exposed in vitro to an LK 3 inducer, followed by recovering the accumulated LK 3 from the culture.

When a conventional-type diffusion chamber is used, exposure of the proliferated human cell to an LK 3 inducer is carried out in the chamber or after harvest therefrom.

The human cell so obtained may be cultured in vitro for an additional 1–4 days to regulate its generation time, prior to induction of LK 3 production.

Production of LK 3 per animal may be further augmented by employing one or more of the following methods:

(1) a method wherein the proliferated human cell is exposed to an LK 3 inducer in the animal, which has been used as the host for the cell proliferation, and then harvested from certain site(s) of the animal or its whole body, followed by in vitro exposure of the human cell to an LK 3 inducer, (2) a method wherein the human cell is repeatedly exposed to an LK 3 inducer, and (3) a method wherein the diffusion chamber embedded in or connected to the animal is replaced at intervals with fresh one.

The LK 3 inducers usable in the invention are conventional IFN-alpha inducers such as virus, nucleic acid and nucleotide: and conventional IFN-gamma inducers such as, phytohemagglutinin, concanavalin A, pokeweed mitogen, lipopolysaccharide, endotoxin, polysaccharide and bacteria. Antigens act on sensitized cell as LK 3 inducer.

Production of LK 3 is augmented by a combined use of IFN-alpha- and IFN-gamma-inducers as LK 3 inducer. It was confirmed that such combination induces a simultaneous production of HuIFN. This is very advantageous in a simultaneous and low-cost mass-production of two or more biologically-active substances, i.e. invaluable LK 3 and HuIFN, as well as in a much more effective utilization of human cells.

The LK 3 so obtained can be recovered by one or more purification and/or separation procedures, for example, salting-out, dialysis, filtration, centrifugation, concentration, and/or lyophilization. If a much more purified LK 3 preparation is desirable, a preparation of the highest purity can be obtained by the above described procedure(s) in combination with other conventional procedure(s), for example, adsorption and desorption with ion exchange, gel filtration, isoelectric point fractionation, electrophoresis, ion exchange chromatography, high-performance liquid chromatography, column chromatography, and/or affinity chromatography.

Immobilized monoclonal antibodies obtained by binding a monoclonal anti-LK 3 antibody onto a suitable waterinsoluble carrier, for example, BrCN-activated Sepharose, a product of Pharmacia Fine Chemical AB, Uppsala, Sweden, can be advantageously used to expedite and facilitate purification of LK 3. The monoclonal anti-LK 3 antibody can be prepared by immunizing a non-human warm-blooded animal with LK 3, recovering the antibody-producing cell from the body of the animal, fusing the antibody-producing cell with a myeloma cell, selecting a clone capable of producing anti-LK 3 antibody, proliferating the clone, and recovering the formed antibody.

It was confirmed that LK 3 thus obtained has the following physicochemical properties:
(1) Molecular weight;
15,000±2,000 daltons
(2) Isoelectric point;
pI=4.5±0.5
(3) Electrophoretic mobility;
on Disc-PAGE, Rf=0.73±0.05
(4) uv-Absorption spectrum; an absorption maximum at a wave length of about 280 nm
(5) Solubility in solvents:
dissoluble in water, saline and phosphate buffer scarcely dissoluble or insoluble in ethyl ether, ethyl acetate or chloroform
(6) Coloring reaction;
protein-positive by the Lowry's method or microburette method saccharide-positive by the phenol-sulfuric acid method or anthrone-sulfuric acid method
(7) Biological activities;
cytostatic on KB cell with or without HuIFN-alpha cytotoxic on L 929 cell substantially free of IL and IFN activities
(8) Stability in aqueous solution;
stable up to 60° C when incubated at pH 7.2 for 30 minutes stable in the pH range of 2.0-11.0 when incubated at 4° C for 16 hours, and
(9) Stability on cryopreservation;
stable at −10° C over a period of one month or longer.

Also was confirmed that LK 3 does not effect any substantial cytolysis on normal human cells, but effects a remarkable cytolysis on a variety of human tumor cells in the presence of HuIFN to kill the cells. Thus, LK 3, for example, in the form of composition, is suitable for prophylactic and/or therapeutic for LK 3-sensitive diseases, for example, malignant tumors, more particularly, those of human origin, treatment of which has been deemed very difficult.

The activity of LK 3 was assayed with either KB cell or L 929 cell as the target cell: When KB cell was used, the cytostatic activity on KB cell was determined in the presence or absence of 20,000 units of HuIFN-alpha (specific activity of $2 \times 10^8$ units/mg protein) according to the method described in *Cancer Chemotherapy Reports Part 3*, Vol. 3, No. 2, Sept. (1972); When L 929 cell was used, the cytotoxic activity on L 929 cell in the presence of actinomycin D was determined by the method described in *Lymphokines*, Vol. 2, pp.245-249, "Tumor Necrosis Factor", edited by E. Pick, published by Academic Press, Inc. (1981). Throughout the SPECIFICATION, the former method using KB cell and HuIFN-alpha was employed unless specified otherwise.

The activity of IL was determined by measuring either IL 1 activity in accordance with the method as reported in Diana Boraschi et al., *The Journal of Immunology*, Vol.133, No.2, Aug. (1984), or IL 2 activity in accordance with the method as reported in Steven Gillis et al., *The Journal of Immunology*, Vol.120, No.6, pp.2027-2032 (1978).

The activity of HuIFN was assayed by the plaquere-duction method using FL cells of human amnion origin described in *Protein, Nucleic Acid and Enzyme*, Vol.20, No.6, pp.616-643 (1975).

The hemagglutination activity was assayed according to the method reported by S. E. Salk, *The Journal of Immunology*, Vol.49, pp.87-98 (1944).

The following Experiments further detail the present invention.

Experiment A-1

Preparation of partially-purified LK 3

Newborn hamsters were injected with a conventional antiserum prepared from rabbit to weaken their immunoreaction, transplanted subcutaneously with a human lymphoblastoid line, BALL-1, and fed in usual way for 3 weeks. The tumor masses, formed subcutaneously, were extracted, minced and disaggregated in saline. The cell suspension so obtained was washed with RPMI 1640 medium (pH 7.2) supplemented with serum, and resuspended in a fresh preparation of the same culture medium to give a cell density of about $2 \times 10^6$ cells/ml. The cell suspension was added with Sendai virus (about 400 hemagglutination titers/ml), and incubated at 37° C for 24 hours to induce LK 3 production.

The culture was centrifuged at about $1,000 \times g$ and about 4° C, and the resultant precipitant was removed. The supernatant so obtained was dialyzed against saline containing 0.01 M phosphate buffer (pH 7.2) for 20 hours, and treated with a membrane filter. The filtrate was then passed through a column of an immobilized anti-HuIFN antibody, and the unadsorbed fraction was collected. An active fraction was recovered from this fraction by means of chromatofocusing, concentrated and lyophilized to obtain a powder product with LK 3 activity.

The specific activity of the product was about $10^5$ units/mg protein. The LK 3 yield was about $1.0 \times 10^6$ units per hamster.

Experiment A-2

Preparation of anti-LK 3 antibody

An LK 3 preparation, obtained by the method in Experiment A-1, was dissolved in saline to give a concentration of about 0.05 w/w % as protein, and the solution was added with the same volume of Freund's complete adjuvant. Mice were immunized by subcutaneously injecting 0.2 ml aliquots of the mixture so obtained, and boosting seven days after the first injection. After inducing anti-LK 3 antibody production in the antibody-producing cell of the animals, the spleens of the animals were extracted, minced, disaggregated and suspended together with a mouse myeloma cell line, $P_3$-X63-Ag8, purchased from Flow Laboratories Inc., Rockville, Maryland, USA, in serum-free Eagle's minimal essential medium (pH 7.2) containing 50 w/v % polyethylene glycol 1000, prewarmed to 37° C, to give respective cell density of $10^4$ cells/ml, followed by 5-minute standing of the resultant mixture. Thereafter, the mixture was diluted 20-times in a fresh preparation of the same culture medium, and the hybridoma cells capable of growing on the hypoxanthine, aminopterin, thymidine containing medium were collected according to the method reported by R. L. Davidson and P. S. Gerald in *Somatic Cell Genetics*, Vol.2, No.2, 175-176 (1976) to select a hybridoma clone capable of producing anti-LK 3 antibody. Mice were transplanted intraperitoneally with the clone in a dosage of about $10^6$ cells per mouse, fed for 2 weeks and sacrificed. The body fluids of the animals, such as ascite fluid and blood, were recovered, centrifuged and salted out with ammonium sulfate, followed by collection of the fractions sedimented at 30-50% saturation. These fractions were dialyzed and subjected to affinitychromatography using an immobilized anti-LK 3 antibody gel obtained by reacting an LK 3 specimen, prepared by the method in Experiment A-1, with BrCN-activated Sepharose at ambient temperature, to obtain an anti-LK 3 antibody fraction which was then dialyzed, concentrated and lyophilized.

The resultant powder product exhibited an immunologically-specific neutralization to the activity of LK 3.

Experiment A-3

Preparation and physicochemical properties of highly-purified LK 3

A partially-purified LK 3 specimen, obtained by the method in Experiment A-1, was subjected to affinitychromatography using an immobilized monoclonal antibody gel, prepared by the method in Experiment A-2, to collect LK 3 fractions which were then dialyzed, concentrated and lyophilized.

The resultant was a highly-purified LK 3 preparation with a specific activity of about $10^7$ units/mg protein.

The physicochemical properties of LK 3 were studied with this preparation.

(1) Molecular weight:

The molecular weight of LK 3 was determined by the electrophoretic methods using SDS-polyacrylamide gel described in K. Weber and M. Osborn, *Journal of Biological Chemistry*, Vol. 244, page 4,406 (1969). Columns of 10% acrylamide gel were loaded with about 10 micrograms aliquots of the preparation in the presence of 0.1% SDS, and charged with 8 mA per column for 4 hours to effect electrophoresis. After extraction and subsequent LK 3 assay of the active fractions, the molecular weight of LK 3 was $15,000 \pm 2,000$ daltons.

(2) Isoelectric point:

A 2 hour, 25 W electrofocusing of the preparation using "AMPHOLINE PAGPLATE (pH 3.5-9.5)", a gel product for electrofocusing, commercialized by LKB-Produkter AB, Stockholm, Sweden, gave an isoelectric point pI of $4.5 \pm 0.5$.

(3) Electrophoretic mobility:

According to the method described in B. J. Davis, *Annals of New York Academy of Sciences*, Vol.121, page 404 (1964), about 10 micrograms aliquots of the preparation were loaded on columns of 7.5% acrylamide gel, subjected to electrophoresis at pH 8.3 and 3 mA per column for 2 hours, extracted and assayed for LK 3 activity to obtain an electrophoretic mobility Rf of $0.73 \pm 0.05$.

(4) uv-Absorption spectrum:

After analyzing the uv-spectrum of the preparation with UV-250 spectrometer, a product of Shimadzu Seisakusho KK, Kyoto, Japan, an absorption maximum was found at a wave length of about 280 nm.

(5) Solubility in solvent:

Dissoluble in water, saline and phosphate buffer solution; scarcely dissoluble or insoluble in ethyl, ethyl acetate and chloroform.

(6) Coloring reaction:

Protein-positive by the Lowry's method and the microburette method; saccharide-positive by the phenol-sulfuric acid method and the anthronesulfuric acid method.

(7) Biological activity:

A cytostatic activity on KB cell with or without HuIFN-alpha, and a cytotoxic activity on L 929 cell were noted. No substantial IL or IFN activity was noted.

(8) Stability in an aqueous solution:

(i) Heat stability:

About $1 \times 10^3$ units/ml aliquots of the preparation were incubated at pH 7.2 and different temperatures for 30 minutes, and the residual activities were assayed. As a result, LK 3 was found stable up to 60° C.

(ii) pH Stability:

0.1 ml aliquots of the preparation ($1 \times 10^4$ units/ml) were added with 1 ml buffer solution of different pH levels, i.e. McIlvaine buffer at pH 2-7; phosphate buffer, pH 7-8; glycine-NaOH buffer, pH 8-11, and incubated at 4° C for 16 hours. Thereafter, 0.1 ml of the incubated mixture was adjusted to pH 7.2 with 0.05 M phosphate buffer (pH 7.2), and the residual activity was assayed. As a result, LK 3 was found stable in the pH range of 2.0-11.0.

(9) Stability to cryopreservation:

The LK 3 preparation was stored in aqueous solution at $-10°$ C and pH 7.2 for one month, thawed and assayed. No decrease in activity was noted.

These evidences revealed that LK 3 had physicochemical properties distinguishable from those of known lymphokines such as LT, TNF, IL or IFN.

Experiment B-1

Cytostatic effect on malignant tumor cells

The cytostatic activity of LK 3 on several human cells was studied with LK 3 preparations obtained by the method in Experiment A-3.

One human cell ($10^6$ cells) listed in Table I was suspended in 1 ml of conventional nutrient culture medium supplemented with fetal calf serum, cultured for 1 day, added with 0.1 ml of a saline containing either 20 units of an LK 3 preparation, prepared by the method in Experiment A-3, or 20 units of the LK 3 preparation and 2,000 units of HuIFN-alpha having a specific activity of $2 \times 10^8$ units/mg protein, and incubated at 37° C for 2 days. After completion of the culture, the viable cell was stained with neutral red, a type of staining agent, according to the method described in *Applied Microbiology*, Vol.22, No.4, pp.671–677 (1971), and the staining agent was eluted with an acidified ethanol solution. The number of the viable cell was determined by measuring the absorbance of the eluate at a wave length of 540 nm.

As the control, 0.1 ml of an LK 3 free saline was used.

Cytostatic rate (%) was calculated with the following equation:

$$\text{Cytostatic rate (\%)} = \left(1 - \frac{\text{Absorbance when } LK \text{ is used}}{\text{Absorbance of the control}}\right) \times 100$$

TABLE I

| Cell line | Source of cell line | Dosage of LK 3 (Dosage of HuIFN-alpha) | | |
|---|---|---|---|---|
| | | 20 units (0 unit) | 0 unit (2,000 units) | 20 units (2,000 units) |
| HEp#2* | Larynx epidermoid carcinoma | 3 | 2 | 48 |
| PC-8* | Lung carcinoma | 2 | 4 | 62 |
| MKN 7* | Gastric cancer | 4 | 1 | 54 |
| HLE* | Liver carcinoma | −1 | −2 | 50 |
| HeLa* | Cervix epithelioid carcinoma | −2 | 1 | 45 |
| L-132** | Embryonic lung | 3 | 2 | 1 |
| Chang liver** | Liver | 2 | −3 | −3 |
| Giradi heart** | Heart | −2 | 1 | 2 |

Note:
*indicates human cell lines of malignant tumor origins;
**those of normal origins.

The results were as shown in Table I.

These results confirmed that LK 3 inhibited extremely along with HuIFN the growth of various malignant tumor cells. Also was confirmed that LK 3 and a highly-purified HuIFN-alpha affected neither normal nor malignant tumor cell.

Experiment B-2

A group of BALB/c nude mice was transplanted subcutaneously in their dorsum areas with small fragments of human breast cancer tissue.

After the tumor masses grew to about 200 mm³ in the bodies of the animals, saline containing an LK 3 preparation, obtained by the method in Experiment A-1 or A-3, was injected intravenously once every day in a dosage of either 50 units/kg or 500 units/kg together with 5,000 units of HuIFN-alpha, specific activity of $2 \times 10^8$ units/mg protein, for 20 days. Thereafter, the animals were sacrificed, and the resultant tumor masses were weighed.

The results were as shown in Table II.

TABLE III

| Treatment | Dosage per day (units/kg) | Tumor mass (g) |
|---|---|---|
| Control | 0 | 10.8 ± 1.0 |
| LK 3 | 50 | 7.0 ± 0.7* |
| at Experiment A-1 | 500 | 6.8 ± 0.6* |
| LK 3 | 50 | 6.7 ± 0.7* |
| at Experiment A-3 | 500 | 6.2 ± 0.5* |

Note:
*means the values statistically significant against the control in a level of significance of 5%.

Experiment B-3

As acute toxicity test, wherein a group of 20-day old mice was administered with an LK 3 preparation, obtained by the method in Experiment A-3, confirmed that the toxicity of the preparation was extremely low, i.e. $LD_{50}$, $10^8$ units or more, upon intraperitoneal injection.

As is obvious from the above experiments, combination of LK 3 and HuIFN is extremely inhibitory on the growth of malignant tumors in vitro as well as in vivo. Administration of LK 3 is very safe in view of its effective dosage.

The effective dosage of LK 3 generally is in the range of 1–100,000,000 units/day for an adult: more particularly, for local administration, for example, in the form of local injection or collyrium, 1–1,000,000 units/day; for percutaneous or permucosal administration, for example, in the form of ointment or suppository, 10–50,000,000 units/day; for systemic administration, for example, intravenous- or intramascular injection, 10–10,000,000 units/day; and oral administration, 50–100,000,000 units/day, but the dosage is freely variable dependent upon the administration method and patient's symptom. Although LK 3 can be prepared into medicine in usual manner after admixing suitably with conventional carrier, base and/or vehicle, the LK 3 content thereof should be at least 1 unit/g in view of its toxicity, effective dosage and safety.

The shape and form of prophylactic- and/or therapeutic agents for LK 3-sensitive diseases can be freely chosen: for example, for oral administration, it may be shaped into preparations for enteric uses, for example, capsule, tablet or powder; for rectal administration, suppository; for injection, it may be, for example, prepared into a lyophilized injection which is dissolved, prior to use, into an injection solution with distilled water, as well as in the forms of collunarium, collyrium or ointment.

In the treatment of a malignant tumor patient, for example, a tumor tissue fragment extracted from the patient may be treated in vitro with LK 3 to enhance the immunogenicity of the tissue fragment, and administered to the patient to obtain a much more effective treatment of the malignant tumor. Combined uses of LK 3 with antioncotic(s), for example, lymphokines such as TNF, LT and ILs; antioncotic polysaccharides such as beta-1,3-glucan, arabinomannan, lipopolysaccharide, picibanil (OK-432), krestin (PSK) and lentinan; metabolic antagonists such as methotrexate (MTX) and fluorouracil (5FU); and antioncotic antibiotics such as doxorubicin (ADM) and mitomycin C (MMC) are very advantageous.

The following Examples A and B are illustrative respectively of LK 3 production, and pharmaceutical compositions containing LK 3.

EXAMPLE A-1

A human lymphoblastoid line, BALL-1, was inoculated on Eagle's minimal essential medium (pH 7.4) supplemented with 20% fetal calf serum, and cultured in vitro in suspension at 37° C in usual manner. The proliferated human cell was then washed with serum-free Eagle's minimal essential medium (pH 7.4), and resuspended in a fresh preparation of the same culture medium to give a cell density of about $1 \times 10^7$ cells/ml. The cell suspension was added with Sendai virus in a dosage of about 1,000 hemmagglutination titers/ml, and incubated at 38° C for 1 day to induce LK 3 production. After centrifuging the resultant culture at about $1,000 \times g$ and about 4° C, the supernatant was dialyzed against saline containing 0.01 M phosphate buffer (pH 7.2) for 15 hours, and treated with a membrane filter. The filtrate was then passed through a column of anti-LK 3 antibody similarly as in Experiment A-1, and the unadsorbed fraction was purified similarly as in Experiment A-3 with affinity chromatography using a column of an anti-LK 3 antibody-bound gel, and concentrated to obtain a concentrate with a specific LK 3 activity of about $10^7$ units/mg protein.

The yield was about $2.0 \times 10^4$ units/liter of the induced cell suspension.

EXAMPLE A-2

Newborn hamsters were injected with a conventional antiserum prepared from rabbit to weaken their immunoreaction, transplanted subcutaneously with a human lymphoblastoid line, BALL-1, and fed for 3 weeks in usual way. The tumor masses, about 15 g each, formed subcutaneously in the animals, were extracted, minced and disaggregated in saline. After washing with serum-free RPMI 1640 medium (pH 7.2), the proliferated cell was resuspended in a fresh preparation of the same culture medium to give a cell density of about $5 \times 10^6$ cells/ml. The cell suspension was added with Sendai virus and E. coli endotoxin in respective dosage of about 1,000 hemagglutination titers/ml and about 10 micrograms/ml, and incubated at 37° C for 1 day to induce LK 3 production. After centrifuging the culture at about $1,000 \times g$ and 4° C to remove the sediment, the supernatant was dialyzed against saline containing 0.01 M phosphate buffer (pH 7.2) for 21 hours, and treated with a membrane filter. The filtrate was purified with a column of antibody similarly as in Example A-1, and the eluate solution was concentrated and lyophilized to obtain a powder product with a specific LK 3 activity of about $10^7$ units/mg protein.

The yield was about $1.5 \times 10^6$ units.

EXAMPLE A-3

Adult nude mice were transplanted intraperitoneally with a human lymphoblastoid line, TALL-1, fed in usual way for 5 weeks, injected intraperitoneally with Newcastle disease virus (about 3,000 hemagglutination titers per nude mouse) which had been substantially preinactivated with uv-irradiation, and sacrificed 24 hours after the injection, followed by harvest of their ascite fluids. The ascite fluids were purified, concentrated and lyophilized similarly as in Example A-2 to obtain a powder product with LK 3 activity.

The yield was about $3.0 \times 10^5$ units per nude mouse.

EXAMPLE A-4

Adult mice were irradiated with about 400 rem of x-ray to weaken their immunoreaction, transplanted subcutaneously with a human lymphoblastoid line, Mono-1, and fed in usual manner for three weeks. The tumor masses, about 10 g each, formed subcutaneously in the animals, were extracted and disaggregated similarly as in Example A-2. The human cell thus obtained was suspended similarly as in Example A-2, after which the resultant cell suspension was added with Sendai virus and concanavalin A in respective dosage of about 500 hemagglutination titers/ml and 0.8 micrograms/ml, and incubated at 37° C for 1 day to induce LK 3 production. Thereafter, the culture was purified, concentrated and lyophilized similarly as in Example A-2 to obtain a powder product with LK 3 activity.

The yield was about $1.0 \times 10^6$ units per mouse.

EXAMPLE A-5

Newborn hamsters were transplanted with a human lymphoblastoid line, Namalwa (ATCC CRL 1432), similarly as in Example A-2, and fed in usual way for 4 weeks. The tumor masses, about 20 g each, formed subcutaneously in the animals, were extracted and disaggregated to obtain a cell suspension having a cell density of about $3 \times 10^6$ cells/ml. The cell suspension was added with Sendai virus in a dosage of about 1,000 hemagglutination titers/ml, and incubated at 36° C for 2 days to induce LK 3 production. The culture was purified and concentrated similarly as in Example A-1 to obtain a concentrate with LK 3 activity.

The yield was about $1.3 \times 10^6$ units per hamster.

EXAMPLE A-6

A human lymphoblastoid line, NALL-1, was suspended in saline, and placed in an about 10 ml cylindrical plastic diffusion chamber equipped with a membrane filter having a nominal pore size of about 0.5 microns. The chamber was embedded intraperitoneally in an adult rat, and the rat was fed in usual manner for 4 weeks. After removal of the chamber, it was found that the cell density in the chamber was about $5 \times 10^8$ cells/ml, which was about $10^2$-fold or higher in comparison with the case of proliferating in vitro in a $CO_2$ incubator using a nutrient culture medium. The human cell was suspended in culture medium similarly as in Example A-2, added with Newcastle disease virus (about 500 hemagglutination titers/ml), which had been preinactivated with uv-irradiation, and phytohemagglutinin (about 50 micrograms/ml), and incubated at 37° C for 1 day to induce LK 3 production. Thereafter, the culture was purified, concentrated and lyophilized similarly as in Example A-2 to obtain a powder product with LK 3 activity.

The yield was about $4 \times 10^5$ units per rat.

EXAMPLE A-7

A human lymphoblastoid line, CCRF-CEM (ATCC CCL 119), was inoculated in the allantoic cavities of embryonated eggs which had been incubated at 37° C for 5 days, and the eggs were further incubated at this temperature for an additional one week. The proliferated human cell was harvested from the eggs, and suspended similarly as in Example A-1 to give a cell density of $5\times 10^6$ cells/ml. The cell suspension was then added with Sendai virus (about 500 hemagglutination titers/ml), and incubated at 37° C for 1 day to induce LK 3 production. The resultant culture was purified and concentrated similarly as in Example A-2 to obtain a powder product with LK 3 activity.

The yield was about $5.0\times 10^5$ units per ten embryonated eggs.

EXAMPLE B-1

Injection

Five hundred thousand units of an LK 3 specimen, prepared by the method in Example A-2, was dissolved in 200 ml saline, and sterilely filtered with a membrane filter. Two ml aliquots of the filtrate was distributed into sterilized glass vials, lyophilized and sealed to obtain an injection powder.

The powder is favorably usable in combination with HuIFN-alpha and/or HuIFN-beta for treating breast cancer, lung carcinoma, liver carcinoma and leukemia.

EXAMPLE B-2

Injection

An injection powder was prepared similarly as in Example B-1, except that $3\times 10^8$ units of HuIFN-alpha derived from a human lymphoblastoid cell was dissolved in 200 ml of saline together with $2\times 10^5$ units of LK 3.

The powder is favorably usable for treating breast cancer, lung carcinoma, liver carcinoma and leukemia.

EXAMPLE B-3

Ointment

An LK 3 specimen prepared by the method in Example A-3, and HuIFN-alpha were kneaded with a minimal amount of liquid paraffin to homogeneity. The mixture was then added with white petrolatum in usual way to obtain an ointment with an LK 3 content of 1,000 units/g and an HuIFN-alpha content of $1\times 10^6$ units/g.

The ointment is favorably usable for treating skin carcinoma, breast cancer and lymphoma.

EXAMPLE B-4

Collyrium

A mixture of 800 ml distilled water, 5 ml beta-phenylethyl alcohol, 100,000 units of an LK 3 specimen prepared by the method in Example A-4, and $1\times 10^7$ units of HuIFNalpha was admixed with sodium chloride in an additional amount of distilled water to obtain 1,000 ml of an isotonic solution.

The solution is favorably usable for treating retinoblastoma.

EXAMPLE B-5

Enteric coated tablet

Enteric coated tablets were prepared according to conventional method by tabletting a mixture of starch, maltose, and an LK 3 specimen prepared by the method in Example A-7 to give an LK 3 content of 200,000 units per tablet (100 mg), followed by coating the tablets with phthalate ester of methyl cellulose.

The tablets are favorably usable in combination with HuIFN-alpha-containing pharmaceuticals for a suitable administration rout to treat colon carcinoma and liver carcinoma.

While the invention has been particularly shown and described with reference to preferred embodiments thereof, it will be understood by those skilled in the art that the foregoing and other changes can be made therein without departing from the spirit and scope of the invention.

We claim:

1. A lymphokine (LK 3), which has the following physicochemical properties:
   (1) Molecular weight;
      15,000±2,000 daltons on electrophoresis using polyacrylamide gel
   (2) Isoelectric point;
      pI=4.5±0.5
   (3) Electrophoretic mobility;
      on Disc-PAGE, Rf=0.73±0.05
   (4) uv-Absorption spectrum;
      an abosrption maximum at a wave length of about 280 nm
   )5) Solubility in solvents;
      dissoluble in water, saline and phosphate buffer scarcely dissoluble or insoluble in ethyl ether, ethyl acetate or chloroform
   (6) Coloring reaction;
      protein-positive by the Lowry's method or microburette method
      saccharide-positive by the phenol-sulfuric acid method or anthrone-sulfuric acid method
   (7) Biological activities;
      cytostatic on KB cell with or without human interferon-alpha, and extremely cytostatic on malignant tumor cells with interferon-alpha cytotoxic on L 929 cell substantially free of interleukin and interferon activities
   (8) Stability in aqueous solution;
      stable up to 60° C when incubated at pH 7.2 for 30 minutes
      stable in the pH range of 2.0–11.0 when incubated at 4° C for 16 hours, and
   (9) Stability on cryopreservation; stable at −10° C over a period of one month or longer.

2. A lymphokine (LK 3 ), made by exposing a human cell capable of producing LK 3 to an LK 3 inducer and recovering the LK 3 so produced; and having the following physicochemical properties:
   (1) Molecular weight:
      15,000±2,000 daltons
   (2) Isoelectric point:
      pI=4.5±0.5
   (3) Electrophoretic mobility:
      on Disc-PAGE, Rf=0.73±0.05
   (4) uv-Absorption spectrum:
      an absorption maximum at a wave length of about 280 nm
   (5) Solubility in solvents:
      dissoluble in water, saline and phosphate buffer;
      scarcely dissoluble or insoluble in ethyl ether, ethyl acetate or chloroform
   (6) Coloring reaction:
      protein-positive by the Lowry's method or microburette method;
      saccharide-positive by the phenol-sulfuric acid method or anthrone-sulfuric acid method
   (7) Biological activities:
      cytostatic on KB cell with or without human interferon-alpha; cytotoxic on L 929 cell; substantially free of interleukin and interferon activities
   (8) Stability in aqueous solution:

stable up to 60° C when incubated at pH 7.2 for 30 minutes;

stable in the pH range of 2,0–11.0 when incubated at 4° C for 16 hours, and (9) Stability on cryopreservation:

stable at −10° C over a period of one month or longer.

3. A pharmaceutical composition, comprising a pharmaceutically-acceptable carrier and an amount of LK 3 effective to inhibit the growth of malignant tumor cells.

4. The composition of claim 3, which contains LK 3 in an amount of at least 1 unit/g of said composition.

5. The composition of claim 3, wherein the form of the composition is selected from the group consisting of injection, collyrium, ointment, suppository and collunarium.

6. The composition of claim 3, which contains an additional lymphokine.

7. The composition in accordance with claim 6, wherein said lymphokine is a human interferon.

8. A pharmaceutical composition, comprising a pharmaceutically-acceptable carrier and an effective amount for inhibiting the growth of malignant human tumors in cooperation with human interferon of LK 3 in accordance with claim 2.

* * * * *